United States Patent [19]

Marlatt

[11] Patent Number: 5,300,016
[45] Date of Patent: Apr. 5, 1994

[54] LOWER LEG SHELF WITH FOLDABLE WEIGHT-BEARING STRUT AND STABILIZER FRAME

[76] Inventor: William W. Marlatt, 11261 N. 75th St., Longmont, Colo. 80503

[21] Appl. No.: 868,463

[22] Filed: Apr. 14, 1992

[51] Int. Cl.$^5$ ............................ A61F 5/01; A61F 2/60
[52] U.S. Cl. .................................... 602/16; 602/26; 602/23; 623/32; 623/28; 135/69
[58] Field of Search .................. 135/68, 69; 602/23, 602/27, 28, 16, 26; 623/28, 27, 38, 32

[56] References Cited

U.S. PATENT DOCUMENTS

| | | |
|---|---|---|
| 875,482 | 12/1907 | Wyatt . |
| 2,778,370 | 1/1957 | Chamblee . |
| 2,827,897 | 3/1958 | Pawlowski ............... 602/23 X |
| 2,832,079 | 4/1958 | Bailey ....................... 623/28 |
| 3,058,120 | 10/1962 | Smith et al. ............... 623/28 |
| 3,272,210 | 9/1966 | Boruvka ................... 602/23 X |
| 4,058,119 | 11/1977 | Rosequist ................. 623/28 X |
| 4,141,375 | 2/1979 | Tykwinski ................ 135/68 X |
| 4,254,948 | 3/1981 | Jacobs . |
| 4,910,927 | 3/1990 | Beatty ...................... 135/68 X |
| 4,924,894 | 5/1990 | Martinez . |

FOREIGN PATENT DOCUMENTS 2193638 2/1988 United Kingdom .............. 135/69

Primary Examiner—Randall L. Green
Assistant Examiner—D. Willse
Attorney, Agent, or Firm—James R. Young

[57] ABSTRACT

A prosthetic device for use as a temporary substitute for a leg that is injured below the knee includes a shelf for supporting the lower leg in a nonweight-bearing position and for supporting the knee in a weight-bearing position. A foldable strut extends below the shelf for supporting a person's weight while standing or walking, and it can be folded to a position adjacent the shelf and lower leg when the person is sitting. A pivotal hinge for connecting the strut to the shelf is skewed in relation to the shelf to position the strut inside the person's lower leg and foot when folded, so it can be used to bear weight as the person rises from a sitting position to a standing position. A stabilizing frame extends upwardly form the shelf for anchoring the prosthetic device to the person's thigh and hip region. Another pivotal hinge connects the stabilizing frame to the shelf. The pivotal hinges are automatically self-latching at positions where the strut and the stabilizing frame are approximately perpendicular to the shelf. These self-latching hinges in combination with the strut that folds to a position alongside the person's foot accommodates hands-free operation while the person is rising from a sitting to a standing position. A weight-bearing handle or hand rest extends upwardly from the stabilizer frame for the person to apply additional stabilizing forces or weight shifting forces with his or her hand.

27 Claims, 7 Drawing Sheets

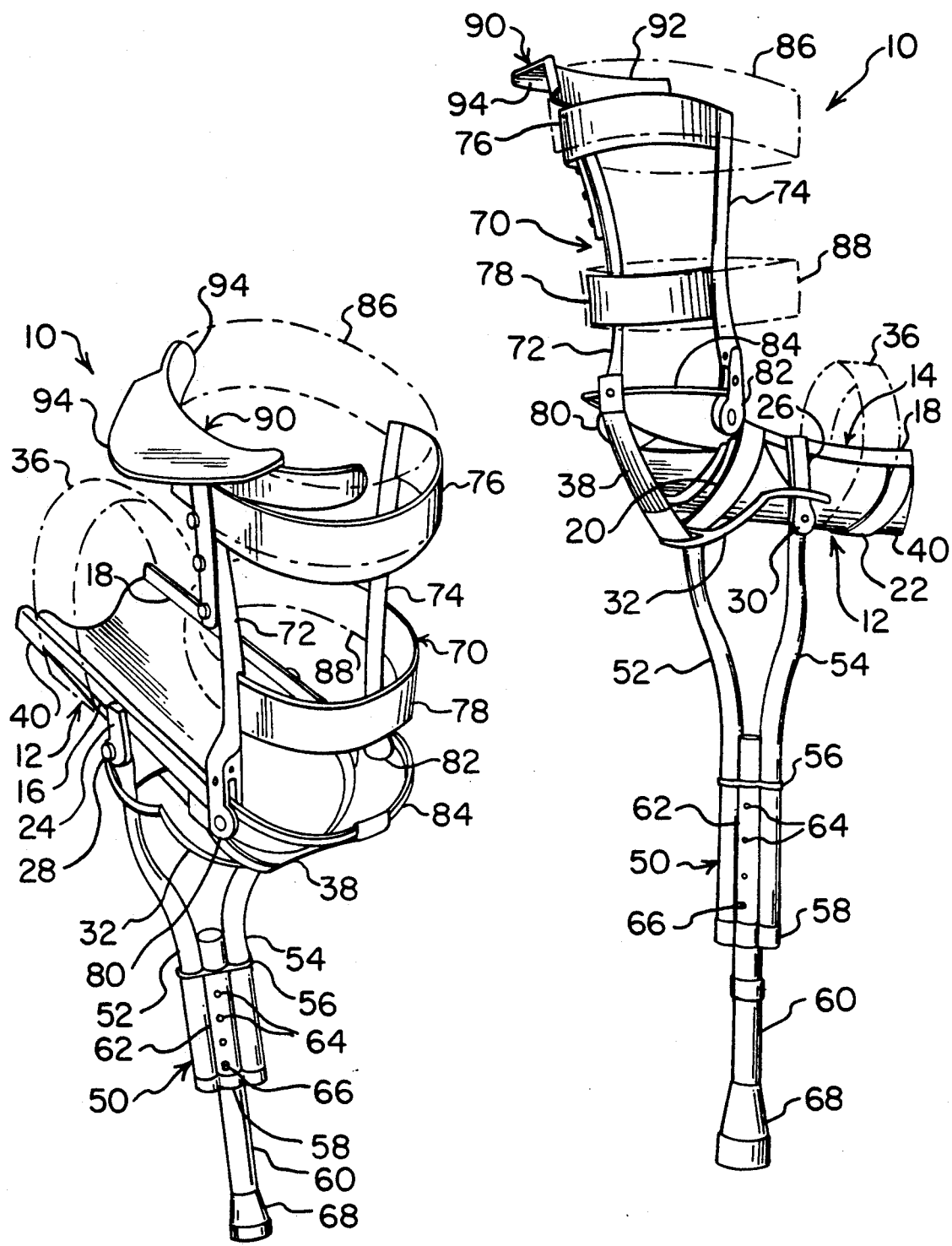

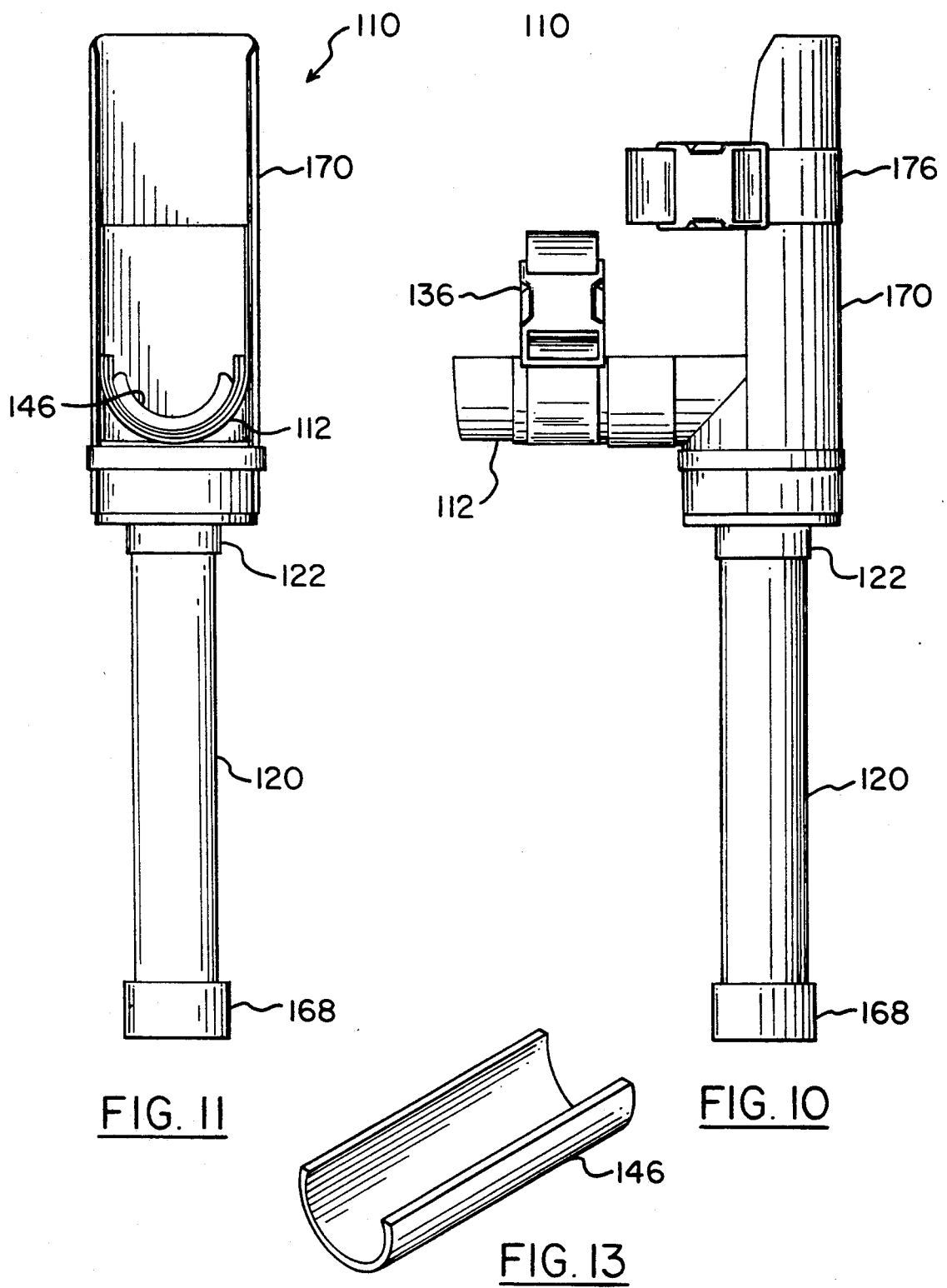

LOWER LEG SHELF WITH FOLDABLE WEIGHT-BEARING STRUT AND STABILIZER FRAME

BACKGROUND OF THE INVENTION

1. Field of the Invention

The present invention is related generally to prosthetic devices and more specifically to a prosthetic device for use as a temporary substitute for a person's lower leg.

2. Description of the Prior Art

When a person suffers a severe traumatic injury to an ankle, foot, or lower leg, he or she usually cannot use the leg for an extended period of time while the injury heals. To be ambulatory during the healing process, some temporary substitute structural device has to be used to support the person's weight that is normally supported by the leg. The conventional and familiar crutch is still the most common such device, and, in many ways, it is still very practical where the injured person just needs to move from one place to another. However, such ordinary crutches occupy the person's hands and arms for manipulating the crutches and for providing needed stability. Therefore, in situations where the person desires to use his or her hands for other purposes while standing or moving around, such as to carry objects or to perform occupational tasks that require the use of hands while standing or walking, conventional crutches are more of a hindrance than a help. Conventional crutches are also usually used in such a manner that they are a complete substitute for the entire leg, even if only the lower leg, ankle, or foot is injured. Therefore, none of a person's weight is borne by any part of the leg, and the natural result is atrophy of the muscles and tissues in the leg.

There have been several prosthetic devices developed that help support the injured person's body weight to improve mobility and comfort over the use of conventional crutches. For example, the U.S. Pat. No. 2,778,370, issued to W. Chamblee, discloses a padded knee support attached to a conventional crutch. Similarly, the U.S. Pat. No. 4,141,375, issued to L. Tykwinski, extended the support for the lower leg and substituted a cane for the crutch. However, neither one of those devices provided a replacement for a crutch or cane that would be stable and secure enough to free both the person's hands for doing other things and also versatile enough to be convenient and comfortable to use for extended period in a wide range of common day-to-day activities, from standing and walking to driving or riding in vehicles to sitting and resting.

The U.S. Pat. No. 4,254,948, issued to E. Jacobs, is even more cumbersome in that it provides a heavy and somewhat complex crank and drive wheel as a substitute for a person's dangling lower leg, which further aggravates the atrophy problem. Both the U.S. Pat. No. 4,924,894, issued to M. Martinez, and U.S. Pat. No. 875,482, issued to W. Wyatt, disclose artificial limbs for amputees, but they really do not accommodate the needs of a temporary prosthetic device where the lower leg is injured and needs time to heal, but is not amputated.

Consequently, despite the above-described developments, there still remains a need for an improved temporary prosthetic device that is more secure, more stable, more versatile, and more comfortable, while it supports a person's injured lower leg in a nonweight-bearing position and while acting as a replacement for bearing the weight of a person's body while standing, walking, and performing routine tasks in situations where the person needs to have his or her hands relatively free to use for other activities.

SUMMARY OF THE INVENTION

Accordingly, it is a general object of the present invention to provide an improved temporary prosthetic device for supporting a person's injured lower leg in a nonweight-bearing position while also supporting the injured person's weight while walking or standing without occupying his or her hands or arms.

A more specific object of this invention is to provide a prosthetic device for supporting a person's lower leg in a nonweight-bearing position and supporting the upper leg in a weight bearing manner, and which also is more comfortable, more versatile, more stable, and more convenient than other similar prosthetic devices.

Additional objects, advantages, and novel features of the invention are set forth in part in the description that follows, and in part will become apparent to those skilled in the art upon examination of the following specification or may be learned by the practice of the invention. The objects and advantages of the invention may be realized and attained by means of the instrumentalities, combinations, and methods particularly pointed out in the appended claims.

To achieve the foregoing and other objects and in accordance with the purposes of the present invention, the temporary prosthetic device includes a shelf for supporting the lower leg in a nonweight-bearing position and the knee and upper leg in a weight bearing manner, a strut extending downwardly from the shelf, and a stabilizing structure extending upwardly for retaining and fastening on the person's upper leg. The strut is foldable from an extended us position perpendicular to the shelf to a folded position adjacent the shelf. The folded position of the strut can be slightly offset from the shelf to avoid the person's foot. The strut can also be adjustable in length. The stabilizing structure can include a rigid outer portion or member that extends upwardly to a position approaching the person's hip and an anchor or hip strap that extends from the rigid outer portion or member around the person's lower torso, opposite hip or waist, and back. The shelf or lower frame portion is also preferably connected pivotally to the stabilizing structure so that it is foldable from a use position substantially perpendicular to the stabilizing structure to a relaxed or folded out position approaching more of a longitudinal alignment with the upper leg and stabilizing structure. Releasable latching hinges can latch these components in their use positions and unlatch them to fold into more relaxed or nonuse positions. Selective cushioning can be used to distribute pressure on the person's knee and lower leg.

BRIEF DESCRIPTION OF THE DRAWINGS

The accompanying drawings, which are incorporated in and form a part of the specifications, illustrate the preferred embodiments of the present invention, and together with the description serve to explain the principles of the invention.

FIG. 4 is a perspective view of the temporary prosthetic device of the present invention from the left front;

FIG. 5 is a perspective view of the temporary prosthetic device of the present invention from the right front;

FIG. 10 is a right side elevation view of an alternate embodiment temporary prosthetic device;

FIG. 11 is a rear elevation view of the alternate embodiment temporary prosthetic device of FIG. 10;

FIG. 13 is a perspective view of the trough insert for cushioning the lower leg;

DETAILED DESCRIPTION OF THE PREFERRED EMBODIMENTS

A temporary prosthetic device 10 according to the present invention is illustrated in FIGS. 1-8. The temporary prosthetic device 10 comprises generally an elongated strut 50 that is designed to replace temporarily an injured lower leg L of a person P, while the lower leg U is held by a shelf 12 in a nonweight-bearing position for healing. A stabilizer structure 70 on the person's upper leg L fastens the prosthetic device 10 securely to the person P and provides lateral stability to the prosthetic device 10 as the person P bears his or her weight on the shelf 12 and strut 50 for standing or walking without a conventional crutch.

Figure 6:
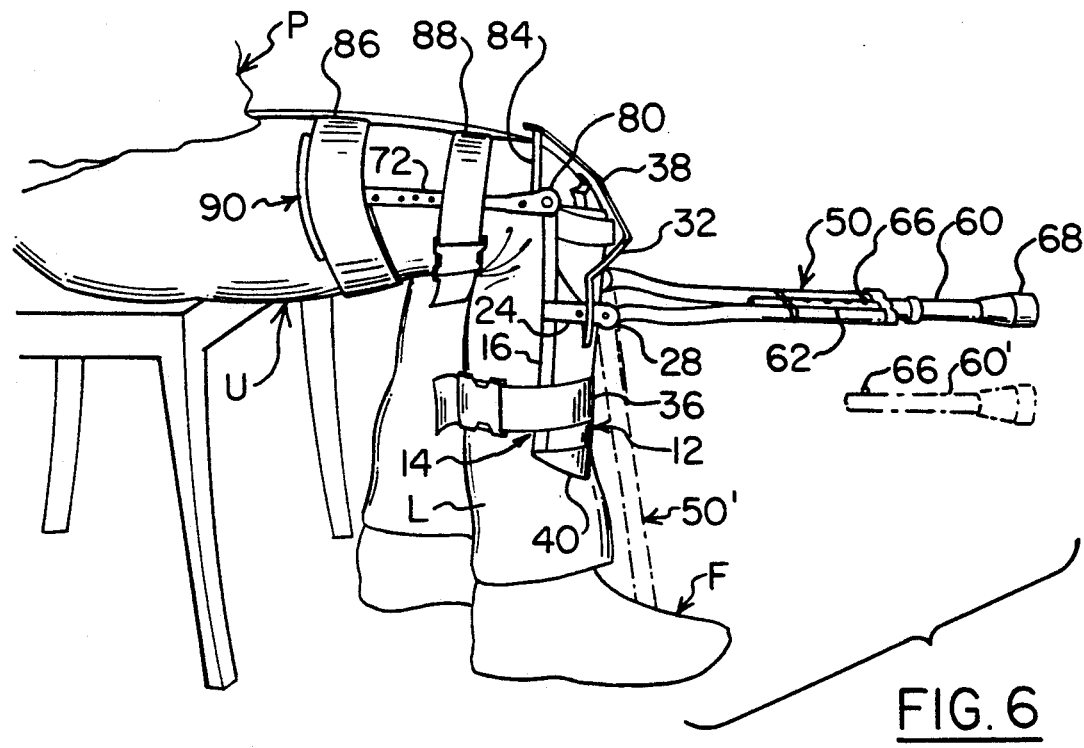
FIG. 6 is a right side elevation view of the temporary prosthetic device of the present invention shown mounted on a person's right leg in sitting position and with the strut folded position of the strut shown in broken lines.

In the preferred embodiment prosthetic device 10, the strut 50 is pivotally attached to the shelf 12, so that it can be pivoted, as shown in FIG. 6, to an alternate position 50, when the person P sits. This folding or pivoting feature of strut 50 accommodates the person P sitting, so that the strut 50 does not protrude in a dangerous or inconvenient manner and so that the person P can sit in close or tight spaces, such as in an automobile, where the protruding strut 50 would not fit otherwise.

Figures 1, 2:
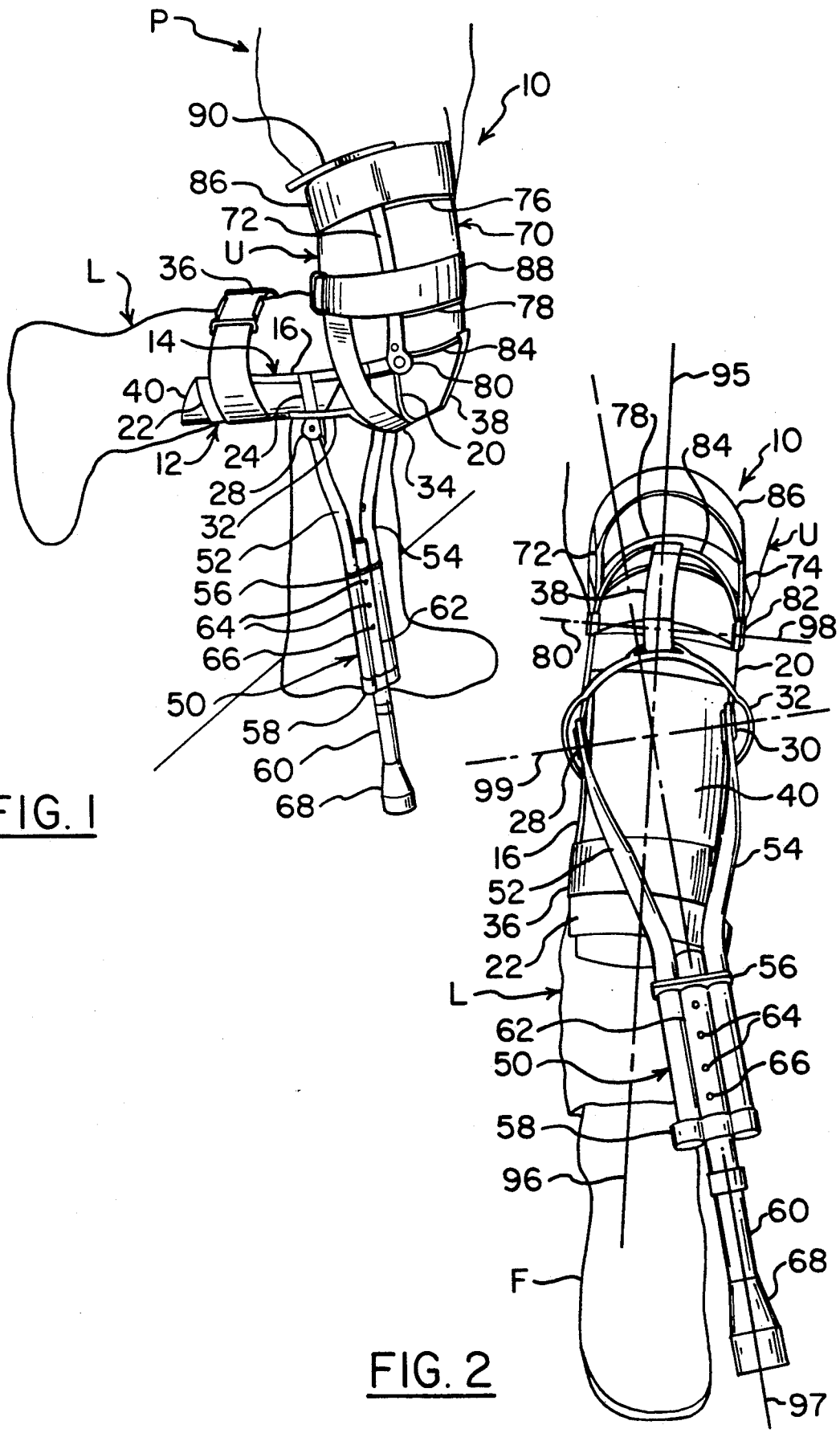
FIG. 1 is a perspective view of the temporary prosthetic device of the present invention mounted on a person's leg in a use position to support the person's weight on his or her knee and upper leg while also supporting an injured lower leg in a nonweight-bearing position.
FIG. 2 is a front elevation view of the prosthetic device of this invention with the person's leg in a sitting position and with the strut unlatched and folded to a position adjacent the lower leg and foot.
Figure 7:
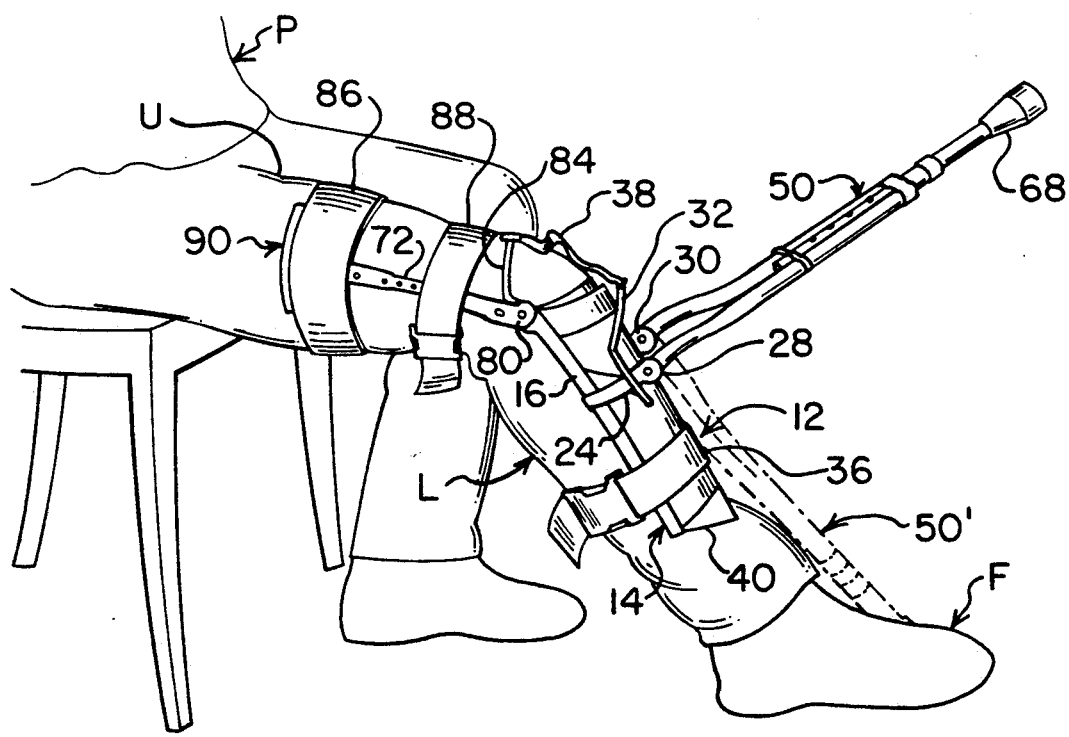
FIG. 7 is a right side elevation view of the temporary prosthetic device of the present invention shown mounted on a person's right leg in a more relaxed sitting position with the latch on the hinges between the lower and upper frames released to allow the lower leg to be partially extended and with the folded position of the strut shown in broken lines.

The preferred embodiment prosthetic device 10 also has the stabilizer frame section 70 pivotally attached to the shelf 12, so the person P can flex or stretch his or her lower leg L while sitting, such as the partially outstretched lower leg position shown in FIG. 7. The strut 50 can also be pivoted downwardly to a position along side the lower leg L and foot F, as shown in FIGS. 2 and 7.

The shelf 12 for holding the injured lower leg L in a nonweight-bearing position bent at the knee about 90 degrees from the upper leg U preferably includes an elongated trough structure 40 mounted in a lower frame 14. The lower frame 14 in the preferred embodiment prosthetic device 10 comprises an elongated outside frame member 16 positioned in substantially parallel, spaced apart relation to a similar elongated inside frame member 18. Two curved cradle members 20, 22 extend between frame members 16, 18 in a downwardly concave configuration for holding the trough-shaped shelf member 40. The proximal end 41 of trough 40 is designed and sized to receive and bear the weight of the person's knee.

The strut 50 in the preferred embodiment prosthetic device 10 comprises a pair of rigid, elongated braces 52, 54 connected to a telescoping adjustable peg 60. The proximal ends of braces 52, 54 are pivotally connected to lower frame 14 by a pair of latching hinges 28, 30. The hinges 28, 30 are mounted on brackets 24, 26 of frame members 16, 18, respectively adjacent the proximal end of shelf 12 where the person's knee is supported. A hollow tube 62 is attached between the respective distal ends of the braces 52, 54 by tying bands 56, 58 and telescopically receives the proximal end of peg 60. A plurality of holes 64 in tube 62 can be used to receive a pin 66 in the proximal end of peg 60 for adjustably fixing the position of peg 60 in tube 62, thereby adjustably fixing the effective length of the strut 50 to match the length of the person's lower leg L for effective and comfortable temporary replacement of the lower leg L as the weight-bearing structure for the person's body while walking or standing.

The hinges 28, 30 are preferably of a type that has a releasable latch mechanism for releasably latching the hinges 28, 30 against pivotal movement when the strut 50 is in substantially perpendicular relation to the shelf member 12, as illustrated in FIGS. 1, 3, 4, and 5. In this latched configuration, the braces 52, 54 cannot pivot in relation to lower frame members 16, 18, so they cannot collapse or fold when bearing the person's weight while standing or walking. However, when the hinges 28, 30 are unlatched, the strut 50 can be folded to a position 50' alongside the person's lower leg L and foot F, as shown in FIGS. 6 and 7, to accommodate the person P sitting without the strut 50 extending in a dangerous or inconvenient manner. Such latching hinges 28, 30 are well known and readily available for prosthetic devices, so they are not considered to be an inventive feature apart from the present invention as a whole.

For enablement purposes the several models of "French Lock" hinged braces, including product numbers 000-231-0040, 000-232-0530, and 000-232-1520, manufactured by United States Manufacturing Company (USMC ™), of Pasadena, Calif., are suitable examples of hinge structures that can be used for the hinges 28, 30. The hinge 28 shown in FIG. 17 can be typical of all the hinges 28, 30, 80, 82 that are used with this invention. It includes a clevis 128, one fork of which is cut away to reveal the functional components, that extends into the hinge bracket 24. It also includes a cam 129 that extends into the brace 52. The cam 129 has a curved cam surface 13 that is abruptly interrupted with a notch 131 and is pivotally mounted on hinge pin 132 such that the clevis 129 and bracket 24 are pivotally attached to the cam 130 and brace 52. A pawl 133 is pivotally mounted on a pin 134 in the clevis 129 for pivotal movement as indicated by arrow 135. A pallet 136 on pawl 133 engages and disengages the notch 131 in cam 129, which locks and unlocks the hinge 28. When the pallet 136 engages the notch 131, the bracket 24 and clevis 129 cannot pivot in relation to the cam 129 and brace 52, thereby locking the hinge 28. On the other hand, when the pawl 133 is moved upwardly to disengage pallet 136 from notch 131, the hinge 28 is unlocked, so the bracket 24 and clevis 129 can pivot in relation to the cam 129 and brace 52 as indicated by the arrow 137. In this unlocked mode, the pallet 136 can ride on the cam surface 130 while the hinge 28 pivots. If the pawl 133 is bias ⓡd downwardly, the pallet 136 will follow the cam surface 130 until the notch 131 becomes aligned with the pallet 136, whereupon the pallet 136 again falls into and engages the notch 131 and again locks the hinge 28. Again, as mentioned above, other lockable hinge structures, such as the "Long Leg Drop" Model 000-212-1520 and similar models manufactured by USMC ™ where a ring or sleeve on the bracket slides over an extension of the brace above the hinge pin, or even removable safety pin that extends through both the bracket and an extension above the hinge pin, could also be used.

Figures 3, 17:
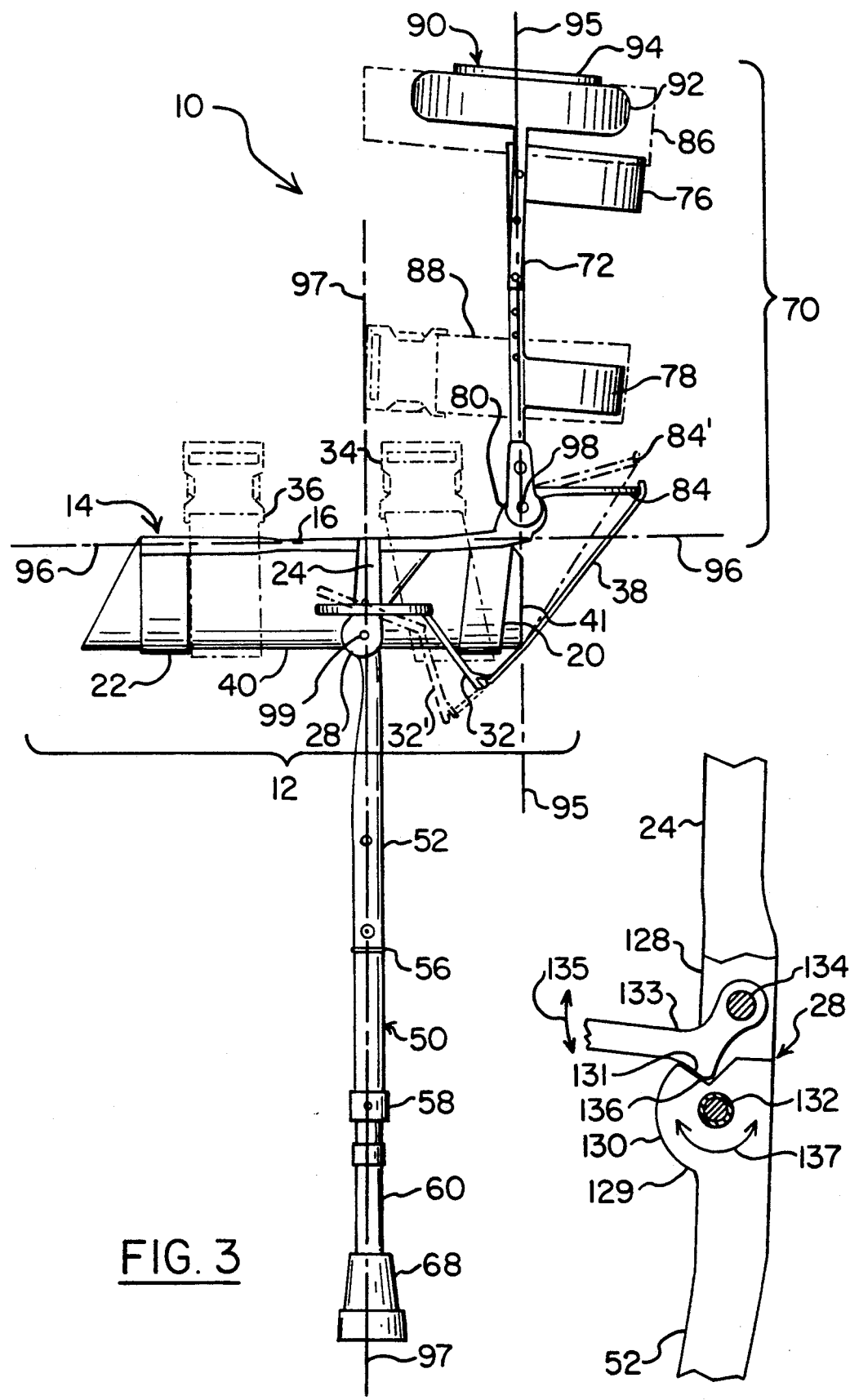
FIG. 3 is a right side elevation view of the temporary prosthetic device of the present invention.
FIG. 17 is an enlarged elevation view of a lockable hinge structure that can be utilized in the implementation of this invention.

A lever actuator or bail 32 is connected to the pawls 133 of both the latch hinges 28, 30 so that it unlatches both the hinges 28, 30 simultaneously when it is manually manipulated to the position 32' shown in FIG. 3. When the hinges 28, 30 are unlatched in this manner, the strut 50 can fold to the position 50', as shown in FIGS. 6 and 7 and as illustrated in FIG. 2. Then, with the lever 32 returned to its original position, which is assured by a bias device, such as the resilient elastic strap 38, as shown in FIG. 3, the strut 50 will latch securely back in its use position perpendicular to shelf 12, when it is manually pivoted to that position by the person P.

The hinges 28, 30 are preferably, but not necessarily, mounted somewhat skewed or cocked, with the outer hinge 28 somewhat lower than inner hinge 30, as shown in FIG. 2. Therefore, when the strut 50 is folded down toward the shelf 40 and lower leg L, it goes toward the inside of the person's foot F, as shown in FIG. 2, so the peg 60 is not obstructed in reaching this folded position by the person's foot. Of course, the hinges 28, 30 could be mounted in a square or symmetrical manner, but the peg 60 would have to be removed as shown in FIG. 6, to allow the strut 50 to reach a fully folded position with no obstruction by the person's foot. It has also been found that this skewed or cocked mounting of hinges 28, 30 and the resulting folded position of the strut 50 in off-axis relation to the person's lower leg L can be beneficial in that it is easier and somewhat more stable for the person to use the strut 50, applying some weight to it, in getting up from a sitting position, even though the hinges 28, 30 are not yet latched in the use position.

The peg 60 is preferably equipped with a skid resistant foot piece 68, such as a rubber plug, at its distal end. The peg 60 can also be removed, as shown in FIG. 6 at position 60,, if the person needs to get the strut 50 into a tight space, such as an automobile (not shown).

The stabilizing upper frame 70 of the prosthetic device 10, as shown in FIGS. 1-8, comprises a pair of upper frame members 72, 74 to fit respectively outside and inside the person's upper leg U. Two rigid, curved tie members 76, 78 extend between outside and inside frame members 72, 74 in a convex outward configuration to form pockets in which the person's upper leg U fits when the upper leg U is positioned between upper frame members 72, 74. The distal ends of outside and inside frame members 72, 74 are pivotally connected respectively to the proximal ends of lower outside and inside frame members 16, 18 by respective outside and inside latch hinges 80, 82. These outside and inside latch hinges 80, 82 can be essentially the same structurally and functionally as the latch hinges 28, 30 described above. They are mounted such that the latched position holds the stabilizing upper frame 70 substantially perpendicular to the shelf member 12, as shown in FIG. 3. Then manual manipulation of a lever 84, which is connected to both latch hinges 80, 82, releases both latch hinges 80, 82 simultaneously to allow the upper frame 70 to pivot in relation to the lower frame 14 of shelf 12, thereby allowing the person P to stretch or extend his or her lower leg L, as shown in FIG. 7. This feature allows the person P to assume a more comfortable, less confining posture, especially while sitting and relaxing.

Figure 8:
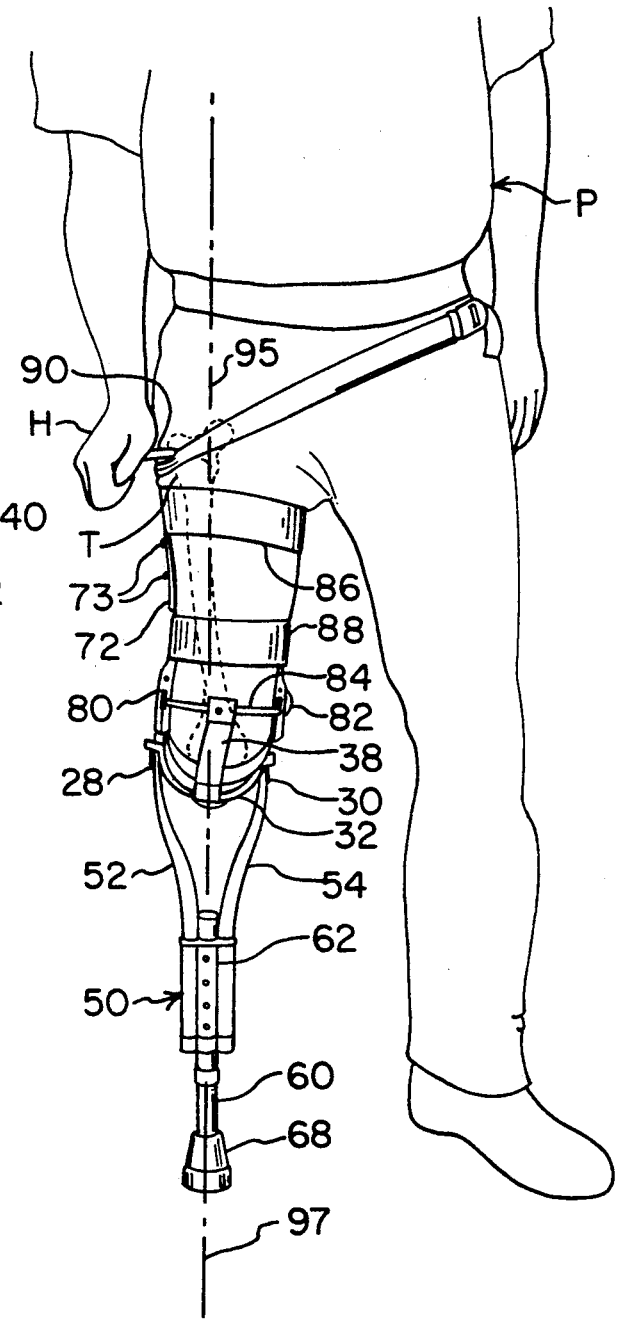
FIG. 8 is a front elevation view of the temporary prosthetic device of the present invention shown with a hip strap for anchoring the upper frame to a person's opposite hip for additional lateral stability and showing the person's hand grasping the handle for additional support.

To further illustrate the relative alignments of the component parts and pivotal structures of the preferred embodiment prosthetic device 10 according to this invention, reference is made to FIGS. 2, 3, and 8. The stabilizing structure 70 is elongated in a manner that defines a stabilizer longitudinal axis 95. Likewise, the shelf structure 12 is elongated in a manner that defines a strut longitudinal axis 96, and the strut 50 is elongated and defines a strut longitudinal axis 97. The stabilizer hinges 80, 82 allow the shelf structure 12 to pivot about a stabilizer pivot axis 98 in relation to the stabilizing structure 70. Likewise, the strut hinges 28, 30 all the strut 50 to pivot about a strut pivot axis 99 in relation to the shelf structure 12.

In the normal, weight-bearing use position, best illustrated in FIGS. 3 and 8, the stabilizer hinges are latched with the stabilizer longitudinal axis 95 approximately perpendicular to the shelf longitudinal axis 96. A person's leg in this position would be bent at the knee approximately 90 degrees with the lower leg resting in and supported by the shelf structure 12, as described above. The stabilizing structure 70 would contain and be secured to the person's upper leg or thigh, as described above, with his or her knee positioned and bearing in the proximal end portion of the shelf structure 12. The strut 50 is latched by strut hinges 28, 30 with the strut longitudinal axis 97 approximately perpendicular to the shelf longitudinal axis 96. Therefore, in this normal use or extended configuration, the strut longitudinal axis 97 is approximately parallel to, but spaced a distance from, the stabilizer longitudinal axis 95, while the shelf longitudinal axis 96 is approximately perpendicular to both the stabilizer longitudinal axis 95 and the strut longitudinal axis 97. Thus, the upward force of the strut 50 is directed into the shelf 12 slightly rearward of, yet approximately parallel to, the downward force of the person's upper leg or thigh, which is approximately aligned with the stabilizer longitudinal axis 95. This orientation tends to distribute some of the person's weight from his or her knee back into the shelf structure 12, as illustrated in FIG. 1, thus enhancing comfort. At the same time, however, those forces are laterally symmetrical through the person's knee and thigh, as best illustrated in the frontal elevation view of FIG. 8, which shows the stabilizer longitudinal axis 95 aligned laterally with the strut longitudinal axis 97, and both of which are aligned laterally symmetrical through the person's knee and thigh. This configuration provides enhanced comfort as well as stability for the person using the prosthetic device 10.

In the folded configuration, however, as best illustrated in FIG. 2, the strut longitudinal axis 97 is skewed and not parallel to either the stabilizer longitudinal axis 95 or the shelf longitudinal axis 96. Thus, it can rest alongside the user's foot F, as shown in FIGS. 2, 6, and 7. This skewed relationship between the strut longitudinal axis 97 in the folded configuration and the stabilizer longitudinal axis 95 and the shelf longitudinal axis 96, while having the benefits of the geometrically perpendicular and parallel alignments described above in the extended use configuration is accomplished with the skewed strut hinges 28, 30. As best seen in FIG. 2, the stabilizer hinges 80, 82 define a pivot axis 98 that is approximately perpendicular to both the stabilizer longitudinal axis 95 and the strut longitudinal axis 96, so that they pivot in relation to each other in a common first plane defined by those axes 95 and 96. When the strut 50 is in its extended use configuration, the strut longitudinal axis 97 is also aligned approximately in that common first plane. However, as also best seen in FIG. 2, the strut pivot axis 99 defined by strut hinges 28, 30 is skewed and not parallel to the stabilizer pivot axis 98 and not perpendicular to either the shelf longitudinal axis 96 or the stabilizer longitudinal axis 95. Therefore, the strut longitudinal axis 97 pivots in a second plane that is skewed to the first plane and ends up in the folded configuration with its distal end 60 nested alongside the person's foot F.

This configuration of the preferred embodiment 10 also enhances the person's ability to rise from a sitting to a standing position, as mentioned above, because the position of the strut 50 alongside the foot allows the user to put some weight on it instead of on his or her foot. Further, as the person rises, the strut 50 applies a vertical force component on the shelf structure 12 through the strut pivot axis 99, which is rearward of the stabilizer pivot axis, as described above, and as best seen in FIG. 3. This vertical force component applied by strut 50 to shelf structure 12 tends to pivot the shelf structure 12 about stabilizer pivot axis 98, thus pushing the shelf structure 12 and the person's lower leg to the perpendicular use position shown in FIGS. 1, 3, and 8. As soon as the shelf structure 12 reaches its use configuration perpendicular to the stabilizer structure 70, the stabilizer hinges 80, 82 lock it in place automatically, as described above. Likewise, as soon as the strut 50 reaches its extended use position perpendicular to shelf structure 12, strut hinges 28, 30 lock it in place automatically, as described above. Thus, essentially hands-free operation rising from a sitting to a standing position is possible.

To further stabilize the stabilizing upper frame 70 and mount it securely to the person's thigh or upper leg U, a pair of elongated flexible straps 86, 88 are provided to encircle and tighten around both the upper frame 70 and the person's upper leg U. They could also have ends fastened to the opposite frame members 72, 74 (not shown), instead of encircling the entire upper frame 70, to the same effect. The straps 86, 88 can, of course, be equipped with any suitable tightenable fasteners, such as buckles, loop and hook fasteners, and the like. The lower frame 14 can be equipped with one or more similar securing straps 34, 36 to secure the person's lower leg L to the shelf member 12.

It is preferred, although not entirely necessary, to further enhance lateral stability of the prosthetic device 10 when mounted on the person's leg to construct the outer frame member 72 of the upper stabilizing frame long enough such that is proximal end reaches up to the person's hip area approximately adjacent the femoral greater trochanter T in the person's upper leg U, as shown in FIG. 8. The greater trochanter T is in a position where it can transfer lateral forces directly to the person's pelvis (not shown), which is a more stable structure of the person's skeleton, so extending the proximal end of outer frame member 72 to this area can help to stabilize the person's body with the prosthetic device 10. An adjustable attachment of the proximal end of frame member 72, such as with removable bolts 73, shown in FIG. 8, or other suitable fasteners, can be used to adjust the effective length of outside frame member 72 to accommodate persons of different height to get this desirable positioning. A curved band or pad 92 is provided at the distal end of outside frame member 72 to more comfortably spread the bearing area of such lateral forces on the person's hip area.

A handle 90, which includes a horizontal bearing piece or palm shelf 94 can also be provided at the proximal end of the outside frame member 72 to accommodate grasping and weight-bearing by a person's hand H on the prosthetic device 10, as illustrated in FIG. 8. This handle 90 allows the person P to use his or her hand and arm to further stabilize and balance his or her body on the prosthetic device 10, as desired, by applying both longitudinal and lateral forces to the upper frame 70. In this way, the prosthetic device can function somewhat like a cane or walking stick while also carrying the function of a prosthetic substitute for a conventional crutch. The prosthetic device 10 as described above is generally sufficiently stable and secure for use without such additional help from the person's hand and arm, but it is not a perfect substitution for the person's lower leg. Therefore, there are times, such as in rougher or more difficult terrain, that this additional feature can be helpful. The handle 90 also provides a suitable rest or comfort position by which the person P can temporarily take some of his or her weight off his or her knee by transferring some of it to his or her arm and upper body.

As also shown in FIG. 8, an anchor type strap 100 extending from the proximal end of outside frame member 72 across the person's lower torso, around his or her opposite hip or waist region, and across his or her lower back can also be provided to further anchor the upper frame 70 to the person's hips and structurally strong portions of the body. This anchor strap 100 can be equipped with a buckle, hook and loop fastener, or any other conventional tightening and fastening device to tighten and secure it around the frame member 72 and around the person's body.

Figure 9:
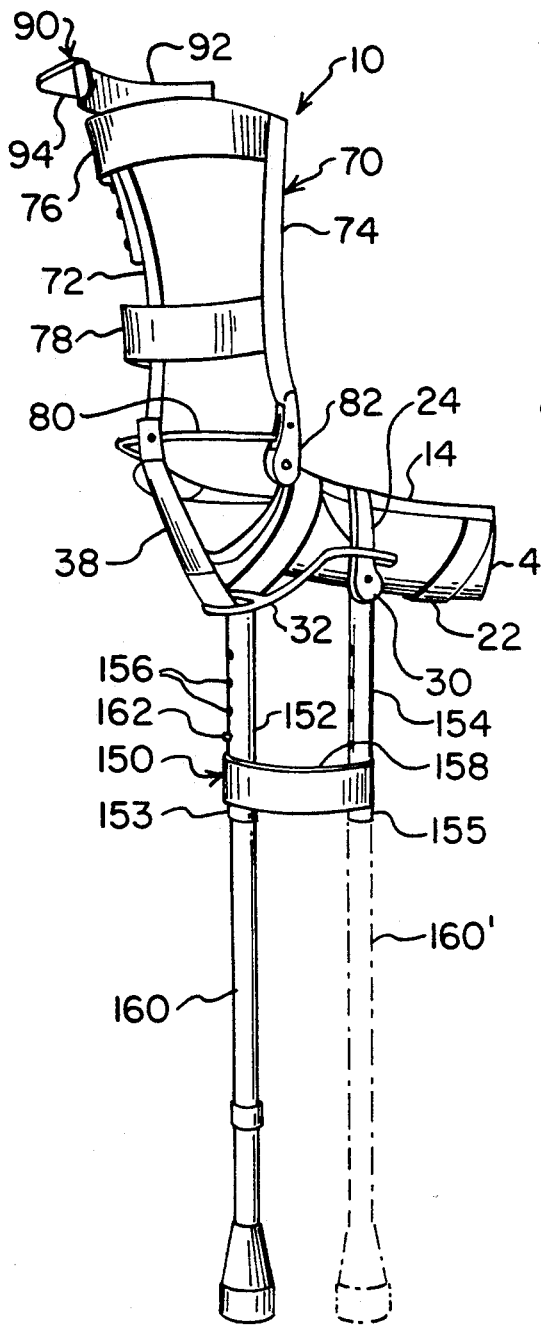
FIG. 9 is a perspective view of an alternate embodiment strut structure of the temporary prosthetic device shown from the left front.

A slightly modified strut 150 is illustrated in FIG. 9. Instead of having the hinges 28, 30 cocked to fold the strut 50 off-axis in relation to the person's lower leg, as described above and shown in FIG. 3, this modified strut 150 in FIG. 9 can be hinged square or symmetrical with the lower frame 14 The two braces 152, 154 do not curve together below the hinges 28, 30, as do the braces 52, 54 of the preferred embodiment strut 50 described above. Instead, they extend substantially straight down, as shown in FIG. 9, and terminate in sockets 153, 155, respectively. These sockets 153, 155 are both adapted to telescopically receive the proximal end of an elongated peg 160. The peg 60 shown in FIG. 9 is adjustably secured in the right brace 152 by a pin 162 in one of a plurality of holes 156 in right brace 152. This mounting is appropriate when the prosthetic device 10 is mounted on the person's right leg. It has the benefit of being foldable somewhat alongside the person's lower leg, because the peg 160 is offset from the centerline of the shelf 40 and the person's lower leg (not shown in FIG. 9). The outwardly curved cross member 158 curves over the shelf 40 and lower leg when the strut 150 is in the folded position.

This offset alignment of peg 160 also has another benefit of causing a force couple when the person's weight is born by the peg 160, which creates a laterally inwardly directed force from the outside frame member 72 onto the person's upper leg. This lateral force on the person's upper leg has to be resisted by the person's body, of course, but it tends to direct more of the person's weight and control to the person's other, noninjured, leg.

The alternate strut 150 embodiment also makes the prosthetic device 10 more versatile in that it can be worn on either leg. If the person injured his or her left leg instead of the right one, the peg 160 can be simply removed from right socket 153 and mounted in left socket 155, as shown in position 160, in FIG. 9.

Figure 12:
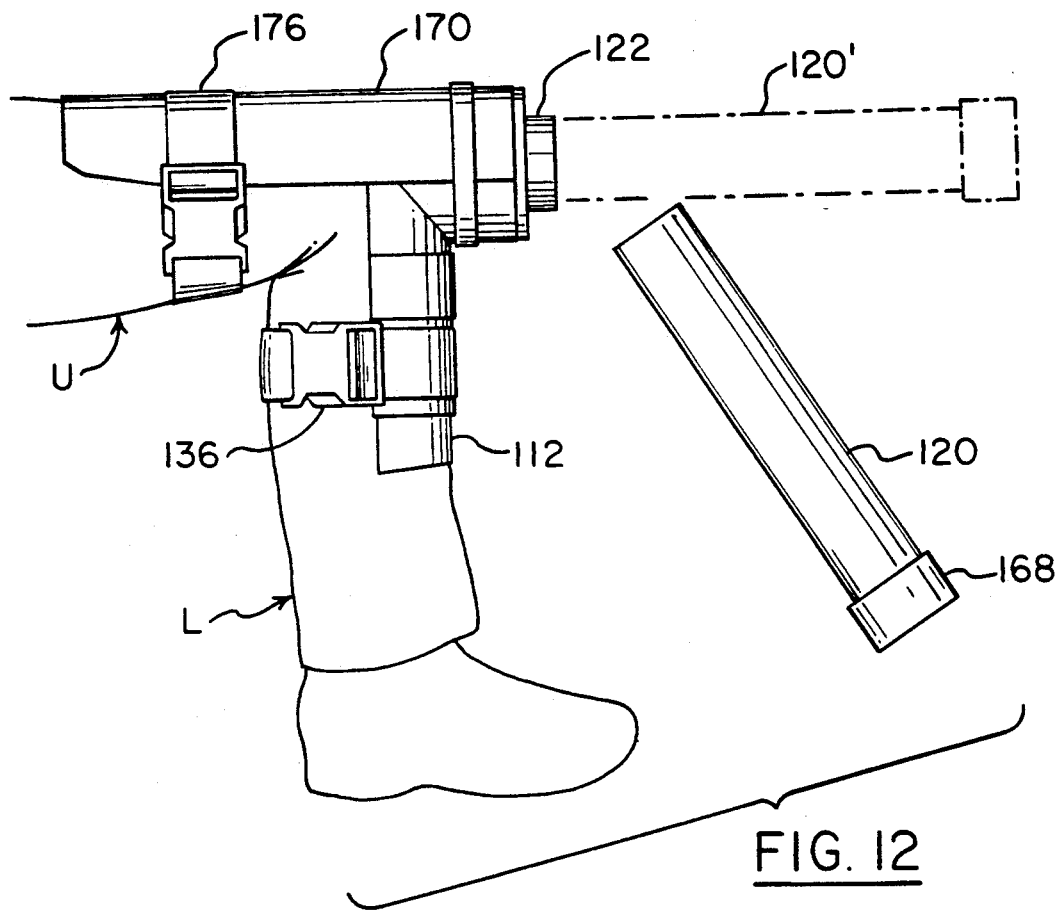
FIG. 12 is a right side elevation view of the alternate embodiment temporary prosthetic device of FIG. 10 mounted on a person's leg in sitting position and with the strut removed.

An alternate embodiment temporary prosthetic device 110 according to this invention is shown in FIGS. 10 and 11. It has a rigid horizontal shelf member 112 or lower frame for holding the person's lower leg in a nonweight-bearing position and a removable strut 120 for bearing the person's weight in place of the lower leg. A stabilizing upper frame 170 is connected rigidly to both the shelf member 112 and strut 120 for receiving and mounting the person's upper leg to the prosthetic device 110. Both the shelf member 112 and the upper frame 170 are trough-shaped to receive the person's leg in a form-fit, comfortable manner. Upper and lower straps 176, 136 secure the respective upper frame 170 and shelf member 112 to the person's upper and lower legs. A socket 122 proximate the intersection of the shelf member 112 with the upper frame member 170 is sized and adapted to removably, but snugly receive the proximal end of strut 120 for removable attachment of the strut 120 to the shelf member 112. Therefore, the strut 120 can be removed from the normal use position 120,, as shown in FIG. 12, when the person sits. A nonslip foot 168 can be attached to the distal end of strut 120.

To enhance the comfort of the person's leg in either the prosthetic device 10 or the alternate embodiment prosthetic device 110, a pressure distributing insert 146, such as the one shown in FIG. 13, can be positioned in the trough-shaped shelf members 40, 112 of the above-described embodiments. Such an insert is preferably also trough-shaped to receive the person's lower leg and knee, and it is preferably a cushioned foam material or a fluid-filled bladder to distribute pressure over a large area of the person's knee and lower leg.

Figures 14, 15, 16:
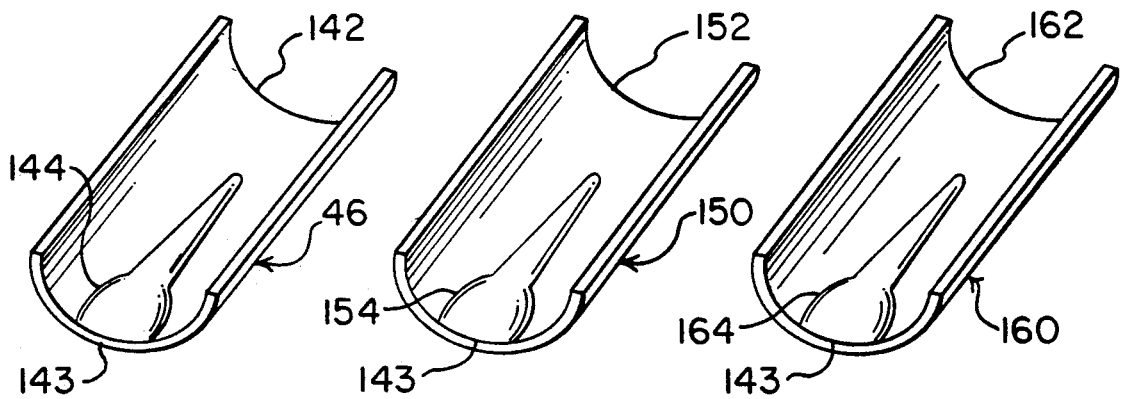
FIG. 14 is a perspective view of an alternate embodiment trough insert with a depression formed therein for the user's knee bone and upper shin.
FIG. 15 is a perspective view of an alternate embodiment trough insert with two different firmness zones.
FIG. 16 is a perspective view of an alternate embodiment trough insert comprising two distinct bladders of different firmness.

An alternative embodiment insert 46 is shown in FIG. 14. It can be custom molded piece that is form fit to an individual person's knee and lower leg, so that a knee bone bearing region 143 has a depression 144 for the person's knee bone and upper shin formed into the remaining portion 142 of the insert 46. Alternatively, as shown in FIG. 15, the knee bone bearing region 143 of an insert 150 can be formed with a material, 154 such as foam, that is more firm or less yielding than less firm foam of the remaining portion 152. Still another alternative is to provide an insert 160 fabricated with two separate, but attached bladders 162, 164, with one bladder 162 filled with a fluid that makes it more firm or less yielding than the fluid filling the other bladder 164.

The foregoing description is considered as illustrative only of the principles of the invention. Further, since numerous modifications and changes will readily occur to those skilled in the art, it is not desired to limit the invention to the exact construction and processes shown as described above. Accordingly, all suitable modifications and equivalents may be resorted to falling within the scope of the invention as defined by the claims which follow.

The embodiments of the invention in which an exclusive property or privilege is claimed are defined as follows:

1. A prosthetic device for attaching to and supporting a person's body utilizing the person's knee, upper leg or thigh, and hips for stability and for supporting the person's lower leg in a nonuse or nonweight-bearing position, comprising:

shelf means with a proximal end portion for supporting the person's knee and upper leg in a weight-bearing position and a distal end portion for supporting the person's lower leg in a nonweight-bearing position and having a shelf longitudinal axis that extends substantially parallel to the person's lower leg when the lower leg is supported by said shelf means;

strut means connected to and extending from said shelf means for supporting said shelf means and for supporting the person's body weight while the person is standing or walking, wherein said strut means has a proximal end and a distal end with a strut longitudinal axis that extends between said proximal end and said distal end;

stabilizing means connected to and extending from said shelf means in substantially an opposite direction from said strut means for stabilizing said shelf means and said strut means by bearing against and transferring lateral forces on said strut means and said shelf means to the person's upper leg and hips, wherein said stabilizing means has a proximal end adapted for positioning adjacent and securing to the person's upper leg and a distal end connected to said proximal end of said shelf means with a stabilizer longitudinal axis that extends between said proximal and distal ends of said stabilizing means and which is approximately parallel to the person's upper leg when the stabilizing means is positioned adjacent and secured to the upper leg;

a stabilizer hinge connecting said proximal end of said shelf means to said distal end of said stabilizing means in such a manner that said shelf means pivots in relation to said stabilizing means about a first pivot axis that is substantially co-axial with the person's knee and perpendicular to both said stabilizer longitudinal axis and said shelf longitudinal axis such that said stabilizer longitudinal axis and said shelf longitudinal axis remain in a common first plane and are pivotal between a first position where the shelf longitudinal axis is approximately perpendicular to the stabilizer longitudinal axis and a second position where the shelf longitudinal axis is approximately collinear with the stabilizer longitudinal axis; and a strut hinge connecting said proximal end of said strut means to said shelf means in such a manner that said strut means pivots in relation to said shelf means about a second pivot axis that is skewed and not in parallel relation to said first pivot axis and not in perpendicular relation to said shelf longitudinal axis such that said strut longitudinal axis pivots in a second plane that is skewed in relation to said first plane from a folded position where the strut longitudinal axis is skewed and neither parallel nor perpendicular to said shelf longitudinal axis to an extended position where said strut longitudinal axis is substantially perpendicular to said shelf longitudinal axis.

2. The prosthetic device of claim 1, wherein said strut hinge includes strut latch means for releasably latching said strut hinge in said extended position and for releasing said strut hinge to fold said strut means in said second plane to said folded position that positions the distal end of said strut means substantially alongside the person's foot.

3. The prosthetic device of claim 2, wherein said strut latch means includes a strut latch mechanism that automatically latches said strut means in said extended position when said strut means is moved to that extended position and a manually operable strut latch release mechanism that unlatches said strut latch mechanism to allow said strut means to be pivoted to said folded position.

4. The prosthetic device of claim 2, wherein said strut means is adjustable in length to position said distal end of said strut means at various distances from said shelf means.

5. The prosthetic device of claim 2, wherein said distal end of said strut means is detachably removable from the proximal end of said strut means.

6. The prosthetic device of claim 1, wherein said stabilizer hinge includes stabilizer latch means for releasably latching said stabilizing means and said shelf means in said first position.

7. The prosthetic device of claim 6, wherein said stabilizer latch means includes a stabilizer latch mechanism that automatically latches said stabilizing means and said shelf means in said first position when said shelf means is moved to that first position and a manually operable stabilizer latch release mechanism that unlatches said stabilizer latch mechanism.

8. The prosthetic device of claim 1, including stabilizer securing means for releasably securing said stabilizing means in substantially immovable relation to the person's upper leg or thigh.

9. The prosthetic device of claim 1, wherein said stabilizing means includes a right lateral outside portion that extends along the outer lateral side of the person's upper leg to an upper end adjacent the person's hip.

10. The prosthetic device of claim 9, wherein said stabilizing means includes a rigid lateral inside portion that extends along the inner lateral side of the person's upper leg.

11. The prosthetic device of claim 10, including pocket means extending between said lateral outside portion and said lateral inside potion and curved convexly outward to accommodate the front of the person's upper leg when the upper leg is positioned between said lateral outside portion and said lateral inside portion of said stabilizing means.

12. The prosthetic device of claim 11, wherein said stabilizer securing means includes an elongated flexible strap that extends from one lateral side of said stabilizing means and around the person's upper leg to the other lateral side of said stabilizing means.

13. The prosthetic device of claim 9, including handle means with a laterally extending member at the upper end of said lateral outside portion of said stabilizing means for accommodating grasping and application of stabilizing vertical and horizontal force vectors to the stabilizing means by the person's hand for additional support.

14. The prosthetic device of claim 13, including anchor means for anchoring said upper end of said stabilizing means to the person's hip.

15. The prosthetic device of claim 14, wherein said anchor means includes a material extending from said upper end of said lateral outside portion of said stabilizing means across the person's lower front torso and lower back and around the person's hip or waist on the opposite side of the person's body from the side where said lateral outside portion is located.

16. The prosthetic device of claim 15, wherein said material includes an elongated, flexible strap.

17. The prosthetic device of claim 1, wherein said shelf means includes an elongated trough structure extending from said proximal end to said distal end for receiving and retaining the person's knee and lower leg.

18. The prosthetic device of claim 17, including cushion material in said trough for cushioning and distributing pressure on the person's knee and lower leg.

19. The prosthetic device of claim 18, wherein a portion of said cushion material in said trough adjacent the proximal end of the shelf means is more firm than the remaining cushion material in said trough.

20. The prosthetic device of claim 19, wherein said cushion material is a resilient foam material and wherein said form material adjacent the proximal end is more dense than the foam material in the remaining portions of said trough.

21. The prosthetic device of claim 18, wherein said cushion material includes an enclosed flexible bladder containing fluid.

22. The prosthetic device of claim 21, wherein said cushion material includes a first bladder adjacent said proximal end of said shelf means and a second bladder in remaining portions of said trough.

23. The prosthetic device of claim 22, wherein said first bladder contains a first fluid and said second bladder contains a second fluid, and wherein said first fluid is one that makes said first bladder more firm than said second fluid.

24. The prosthetic device of claim 1, including lower securing means for releasably securing said shelf means in substantially immoveable relation to the person's lower leg.

25. The prosthetic device of claim 1, wherein said strut means is pivotally connected to said shelf means at a distance spaced from the proximal end of the shelf means toward, but not midway to, the distal end of the shelf means.

26. A prosthetic device for attaching to and supporting a person's body utilizing the person's knee, upper leg or thigh, and hips for stability and for supporting the person's lower leg in a nonuse or nonweight-bearing position, comprising:
- shelf means for supporting a person's lower leg in a nonweight-bearing position, said shelf means having a proximal end and a longitudinal axis that extends substantially parallel to the person's lower leg when the lower leg is supported by said shelf means;
- strut means connected to and extending from said shelf means for supporting said shelf means and for supporting the person's body weight while the person is standing or walking, wherein said strut means has a proximal end and a distal end with a longitudinal axis that extends between said proximal end and said distal end;
- stabilizing means connected to and extending from said shelf means in substantially an opposite direction from said strut means for stabilizing said shelf means and said strut means by bearing against and transferring lateral forces on said strut means and said shelf means to the person's upper leg and hips, wherein said stabilizing means has a proximal end adapted for positioning adjacent and securing to the person's upper leg and a distal end connected to said proximal end of said shelf means with a stabilizer longitudinal axis that extends between said proximal and distal ends of said stabilizing means and which is approximately parallel to the person's upper leg when the stabilizing means is positioned adjacent and secured to the upper leg;
- a stabilizer hinge connecting said proximal end of said shelf means to said distal end of said stabilizing means in such a manner that said shelf means pivots in relation to said stabilizing means about a first pivot axis that is substantially co-axial with the person's knee between a first stabilizer position where the shelf longitudinal axis is approximately perpendicular to the stabilizer longitudinal axis and a second stabilizer position where the shelf longitudinal axis is approximately collinear with the stabilizer longitudinal axis, said stabilizer hinge means including stabilizer latch means for automatically latching said stabilizer hinge means to prohibit pivotal movement when said stabilizing means is moved into said first stabilizer position and stabilizer latch release means for manually releasing said stabilizer latch means; and
- a strut hinge connecting said proximal end of said strut means to said shelf means in such a manner that said strut means pivots in relation to said shelf means about a second pivot axis from a folded position in which said strut means is adjacent the shelf means to an extended position in which said strut longitudinal axis is substantially perpendicular to said shelf longitudinal axis, said strut hinge means including strut latch means for automatically latching said strut hinge means to prohibit pivotal movement when said strut means is moved into said extended position and strut latch release means for manually releasing said strut latch means.

27. The prosthetic device of claim 26, wherein said stabilizer latch release means includes a stabilizer latch release lever for manually releasing said stabilizer latch means, and wherein said strut latch release means includes a strut latch release lever for manually releasing said strut latch means, said stabilizer latch release lever being biased to a latched position, and said strut latch release lever being biased to latched position, wherein said latched position for said stabilizer latch release lever is in a direction substantially toward said strut latch release lever, and wherein said latched position for said strut latch release lever is in a direction substantially toward said stabilizer latch release lever, and including a resilient bias member connecting said stabilizer latch release lever and said strut latch release lever for yieldingly biasing said stabilizer latch release lever toward said strut latch release lever.

* * * * *

UNITED STATES PATENT AND TRADEMARK OFFICE
CERTIFICATE OF CORRECTION

PATENT NO. : 5,300,016
DATED : April 5, 1994
INVENTOR(S) : William W. Marlatt

It is certified that error appears in the above-indentified patent and that said Letters Patent is hereby corrected as shown below:

In the Abstract:

Line 14, change "form" to --from--.

In column 2, line 38, change "us" to --use--.

In column 4, line 7, change "50" to --50'--.

In column 5, line 15, change "13" to --130--.

In column 5, line 32, change "bias 'd" to --biased--.

In column 6, line 10, after "60," delete --,--.

In column 6, line 49, change "all" to --allow--.

In column 8, line 20, change "is" to --its--.

In column 9, line 8, after "14" insert --.--.

UNITED STATES PATENT AND TRADEMARK OFFICE
CERTIFICATE OF CORRECTION

PATENT NO. : 5,300,016
DATED : April 5, 1994
INVENTOR(S) : William W. Marlatt

It is certified that error appears in the above-identified patent and that said Letters Patent is hereby corrected as shown below:

In column 9, line 15, change "peg 60" to --peg 160--.

In column 9, line 40, change "160" to --160'--.

In column 9, line 61, change "120,," to --120',--.

In column 10, line 13, after "material" delete --,-- and after "154" insert --,--.

In column 11, line 29, after "strut" insert --hinge--.

In column 11, line 66, change "right" to --rigid--.

In column 14, line 34, after "to" insert --a--.

Signed and Sealed this

Thirteenth Day of December, 1994

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,300,016

DATED : April 5, 1994

INVENTOR(S) : William W. Marlatt

Page 1 of 2

It is certified that error appears in the above-indentified patent and that said Letters Patent is hereby corrected as shown below:

On the title page item [57],

Line 14, change "form" to --from--.

column 2, line 38, change "us" to --use--.

column 4, line 7, change "50" to --50'--.

column 5, line 15, change "13" to --130--.

column 5, line 32, change "bias@d" to --biased--.

column 6, line 10, "60.," should read --60',--.

column 6, line 49, change "all" to --allow--.

column 8, line 20, change "is" to --its--.

column 9, line 8, after "14" insert --.--.

UNITED STATES PATENT AND TRADEMARK OFFICE
CERTIFICATE OF CORRECTION

PATENT NO. : 5,300,016
DATED : April 5, 1994
INVENTOR(S) : William W. Marlatt

It is certified that error appears in the above-indentified patent and that said Letters Patent is hereby corrected as shown below:

column 9, line 15, change "peg 60" to --peg 160--.

column 9, line 40, change "160" to --160'--.

column 9, line 61, change "120,," to --120',--.

column 10, line 13, after "material" delete --,-- and after "154" insert --,--.

Signed and Sealed this

Tenth Day of January, 1995

Attest:

BRUCE LEHMAN

Attesting Officer

Commissioner of Patents and Trademarks